United States Patent [19]

Goldfine et al.

[11] Patent Number: 5,966,011
[45] Date of Patent: Oct. 12, 1999

[54] APPARATUS FOR MEASURING BULK MATERIALS AND SURFACE CONDITIONS FOR FLAT AND CURVED PARTS

[75] Inventors: Neil J. Goldfine, Newton; David C. Clark, Arlington; Homer D. Eckhardt, Lincoln, all of Mass.

[73] Assignee: Jentek Sensors, Inc., Watertown, Mass.

[21] Appl. No.: 09/122,980

[22] Filed: Jul. 27, 1998

Related U.S. Application Data

[62] Division of application No. 08/702,276, Aug. 23, 1996, Pat. No. 5,793,206.
[60] Provisional application No. 60/002,804, Aug. 25, 1995.
[51] Int. Cl.[6] .......................... G01N 27/72; G01N 27/82; G01R 33/12
[52] U.S. Cl. .......................... 324/242; 324/239; 324/243
[58] Field of Search .......................... 324/207.17–207.19, 324/207.26, 209, 229–233, 239–243; 336/200, 206, 223, 232; 340/870.31, 870.32, 870.35, 870.36

[56] References Cited

U.S. PATENT DOCUMENTS

| | | | |
|---|---|---|---|
| 3,249,854 | 5/1966 | Nevius | 323/108 |
| 3,721,859 | 3/1973 | Blanyer | 317/5 |
| 3,939,404 | 2/1976 | Tait | 324/40 |
| 4,058,766 | 11/1977 | Vogel et al. | 324/61 |
| 4,355,300 | 10/1982 | Weber | 340/146.3 |
| 4,399,100 | 8/1983 | Zsolnay et al. | 422/62 |

(List continued on next page.)

FOREIGN PATENT DOCUMENTS

| | | |
|---|---|---|
| 0 723 166 A1 | 7/1996 | European Pat. Off. . |
| 502205 | 4/1976 | U.S.S.R. . |
| 578609 | 10/1977 | U.S.S.R. . |
| 894547 | 12/1981 | U.S.S.R. . |
| 1095101 A | 5/1984 | U.S.S.R. . |

OTHER PUBLICATIONS

Goldfine, Neil et al., "Dielectrometers and magnetometers, suitable for in–situ inspection of ceramic and metallic coated components," SPIE Conference, Jun. 1995, 6 pages.

Goldfine, Neil et al., "A New Eddy–Current Based Technology for Repeatable Residual Stress and Age Degradation Monitoring," ASNT International Chemical and Petroleum Industry Inspection Technology IV, Houston, TX Jun. 19–22, 1995, 3 pages.

Krampfner, Yehuda D. et al., "Flexible Substrate Eddy Current Coil Arrays," Review of Progress in Quantitative Nondestructive Evaluation, vol. 7A, 1988, pp. 461–478.

Zaretsky, M., et al., "Model Approach to Obtaining Continuum Properties From Inter–Digital Electrode Dielectrometry," Massachusetts Institute of Technology, Lees Technical Report, Jul. 1986, pp. 1–43.

Dodd, V.C. and Deeds, W.E., "Absolute Eddy–Current Measurement of Electrical Conductivity," From "Review of Progress in Quantitative Nondestructive Evaluation," vol. 1, 1981, pp. 387–394.

(List continued on next page.)

*Primary Examiner*—Gerard Strecker
*Attorney, Agent, or Firm*—Hamilton, Brook, Smith & Reynolds, P.C.

[57] ABSTRACT

A meandering winding magnetometer (MWM) includes a meandering primary winding and at least one sensing winding or coil on a membrane to be pressed against a test surface. The membrane may be supported on a flexible carrier which is translatable into a probe. Abutments in the probe press the carrier against the test surface but allow the carrier and membrane to conform to the test surface. One MWM circuit includes meandering primary and secondary windings. The return leads from the secondary winding return to connector pads in close alignment with the test array, while leads from the primary winding are spaced at least one wavelength from the array. In another MWM circuit, individual sensing loops are positioned within the meandering primary winding. The MWM circuit may be provided on an adhesive tape which may be cut to length.

12 Claims, 17 Drawing Sheets

U.S. PATENT DOCUMENTS

| | | | |
|---|---|---|---|
| 4,417,208 | 11/1983 | Hachtel et al. | 324/164 |
| 4,423,371 | 12/1983 | Senturia et al. | 324/61 |
| 4,496,697 | 1/1985 | Zsolnay et al. | 526/60 |
| 4,697,144 | 9/1987 | Howbrook | 324/207.17 |
| 4,757,259 | 7/1988 | Charpentier | 324/227 |
| 4,799,010 | 1/1989 | Muller | 24/240 |
| 4,810,966 | 3/1989 | Schmall | 324/207 |
| 4,814,690 | 3/1989 | Melcher et al. | 324/61 |
| 4,853,617 | 8/1989 | Douglas et al. | 324/67 |
| 4,883,264 | 11/1989 | Yoshikawa et al. | 271/110 |
| 4,922,201 | 5/1990 | Vernon et al. | 324/236 |
| 5,015,951 | 5/1991 | Melcher | 324/232 |
| 5,041,785 | 8/1991 | Bogaerts et al. | 324/207 |
| 5,059,902 | 10/1991 | Linder | 324/207 |
| 5,086,274 | 2/1992 | Gobin et al. | 324/239 |
| 5,182,513 | 1/1993 | Young et al. | 324/232 |
| 5,204,621 | 4/1993 | Hermann et al. | 324/207.18 |
| 5,237,271 | 8/1993 | Hedengren | 324/232 |
| 5,262,722 | 11/1993 | Hedengren et al. | 324/242 |
| 5,293,119 | 3/1994 | Podney | 324/242 |
| 5,315,234 | 5/1994 | Sutton, Jr. et al. | 324/242 |
| 5,345,514 | 9/1994 | Mahdavich et al. | 382/8 |
| 5,363,051 | 11/1994 | Jenstrom et al. | 324/661 |
| 5,373,245 | 12/1994 | Vranish | 324/662 |
| 5,389,876 | 2/1995 | Hedengren et al. | 324/242 |
| 5,434,504 | 7/1995 | Hollis et al. | 324/207.17 |
| 5,442,347 | 8/1995 | Vranish | 340/870.37 |
| 5,453,689 | 9/1995 | Goldfine et al. | 324/239 |
| 5,523,683 | 6/1996 | Okamoto et al. | 324/207.17 |
| 5,541,510 | 7/1996 | Danielson | 324/233 |

OTHER PUBLICATIONS

Dodd, C.V. and Simpson, W.A., "Measurement of Small Magnetic Permeability Changes by Eddy Current Techniques," presented at the National Fall Conference of the American Society for Nondestructive Testing, Oct. 19–22, 1970, pp. 217–221.

Rose J.H. and Nair, S.M., "Exact recovery of the DC electrical conductivity of a layered solid," Inverse Problems, Letter to the Editor, 1991, pp. L31–L36.

Auld, B.A. et al., "Eddy–Current Signal Analysis and Inversion for Semielliptical Surface Cracks," Journal of Nondestructive Evaluation, vol. 7, No. 1/2, 1988, pp. 79–84.

APPARATUS FOR MEASURING BULK MATERIALS AND SURFACE CONDITIONS FOR FLAT AND CURVED PARTS

RELATED APPLICATIONS

This application is a Divisional of Ser. No. 08/702,276, filed Aug. 23, 1996, which issued on Aug. 11, 1998 as U.S. Pat. No. 5,793,206 and which claims benefit of provisional application Ser. No. 60/002,804, filed Aug. 25, 1995, the entire teachings of which are incorporated herein by reference.

BACKGROUND OF THE INVENTION

The technical field of this invention is that of nondestructive materials characterization, particularly quantitative, model-based measurement of bulk material and surface condition for flat and curved parts. Measurement of bulk material condition includes measurement of changes in material state caused by fatigue damage, plastic deformation assessment, residual stress, applied loads, and processing conditions. It also includes measurement of material states such as porosity, alloy type, moisture content and temperature. Measurement of surface condition includes roughness, displacement of relative position, coating thickness and coating condition. Each of these also include detection of electromagnetic property changes associated with the presence of single or multiple cracks.

The methods for measurement include the use of quasistatic fields, electromagnetic (magnetometers and dielectometers) or thermal, that are described by diffusion equations, as opposed to alternative techniques that are described by wave equations. For example, magnetometers have been used to measure foil thicknesses, characterize coatings, and measure porosity, as well as to measure material property profiles as a function of depth into a part, as disclosed in U.S. Pat. Nos. 5,015,951 and 5,453,689. Dielectometers with multiple electrode spacings have been used to measure profiles of properties such as moisture and porosity using methods disclosed in U.S. Pat. No. 4,814,690.

SUMMARY OF THE INVENTION

The present invention relates to a novel apparatus for carrying a test circuit such as a magnetometer or dielectometer to enable that test circuit to conform to a test surface and to novel meandering winding magnetometer (MWM) test circuits.

In accordance with one aspect of the invention, a sensing apparatus comprises a test circuit which imposes a magnetic field on a test substrate and senses a response of the test substrate. The preferred test circuit is a meandering winding magnetometer in which the winding imposes a magnetic field having a periodic spatial wavelength. The test circuit is supported on a flexible carrier. The carrier protrudes from a case such that the test circuit is exposed to a test substrate and is slidable into the case. The case has an abutment for pressing the flexible carrier and the test circuit against the test substrate as the carrier slides into the case, and the carrier flexes to conform to the test substrate. Preferably, the circuit is formed on a flexible membrane which is retained against the surface of the flexible carrier, and the carrier is supported by a rigid holder. The holder is itself slidable within the case and retains the carrier at its center as the abutment abuts opposite sides of the carrier. Preferably, the holder is pivotable about an axis which extends parallel to the side to side dimension.

In accordance with another aspect of the invention, a test circuit comprises a meandering primary winding for imposing a magnetic field in a test substrate, the winding having extended portions across a sensing region and connecting portions joining adjacent extended portions. At least one meandering sensing winding parallels the primary winding. Terminal leads provide a pair of analyzer connections to each of the primary and sensing windings. First and second leads from the at least one sensing winding are closely parallel to each other at a terminal end thereof, and one of the first and second leads includes a return length which closely parallels outer portions of the sensing winding, that is a first extended length of the winding and the connecting portions of the sensing winding. The leads should be spaced no more than one quarter wavelength from each other and the connecting portions.

A second sensing winding may be provided on an opposite side of the primary winding, and the lead pairs from the respective sensing windings are spaced substantially the same distance, at least one wavelength, to opposite sides of a primary winding lead. A second primary winding lead is displaced from the winding array and from the sensing leads by at least one wavelength. Preferably, the connecting portions of the sensing windings and the leads are covered by at least one shield in a plane parallel to the test circuit, in the area outside the sensing region only.

In accordance with another aspect of the invention, another test circuit comprises a meandering primary winding for imposing a spatially periodic magnetic field in a test substrate, the winding having extended portions across a sensing region and coupling portions joining adjacent extended portions. A plurality of individual sensing coils are positioned between respective adjacent extended portions of the primary winding. In one form, a single loop sensing coil is positioned between each pair of extended portions, and in another form, a meandering sensing winding is positioned to one side of the primary winding and individual loops are positioned to the other side of the primary winding. In a third form several meandering sensing windings are included, each covering more than half a wavelength within the sensing region. As taught in U.S. Pat. No. 5,453,689, the response of a substrate to the imposed field is modelled to provide estimates of the substrate properties. The loops are preferably spaced at least one wavelength from the connecting portions of the primary winding to minimize unmodelled coupling to regions of the primary winding. Preferably, a shield in a plane parallel to the test circuit covers the ends of the sensing coils and primary winding.

The test circuit may be formed on a roll of adhesive tape which may be cut at appropriate lengths for an appropriate number of winding turns and sensing coils for particular application. Bonding pads, such as solder pads, are provided to each sensing coil and on each turn of the primary winding. Extra pads may be provided for connections to shield planes and the like.

Either test circuit may be scanned across a test surface. For improved resolution during scanning, adjacent test circuits may be provided, offset by one quarter wavelength.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The purpose of the device of FIGS. 1–5 and the alternative device of FIGS. 6–9 is: (1) to provide support for a thin, flexible, but otherwise practically inextensible (not stretchable) membrane which carries on its surface, or within it, a geometric pattern in a plane parallel to the surface of the membrane; and (2) to provide means for pressing this membrane and its associated pattern into nearly uniformly intimate contact with a variety of firm, convex, developable surfaces of nearly constant radius of curvature (e.g., cones and cylinders). In the current embodiment, the geometric pattern consists of narrow lines of copper foil which is sandwiched between two thin sheets of Kapton® plastic film and the plastic film constitutes the membrane.

Figure 1:
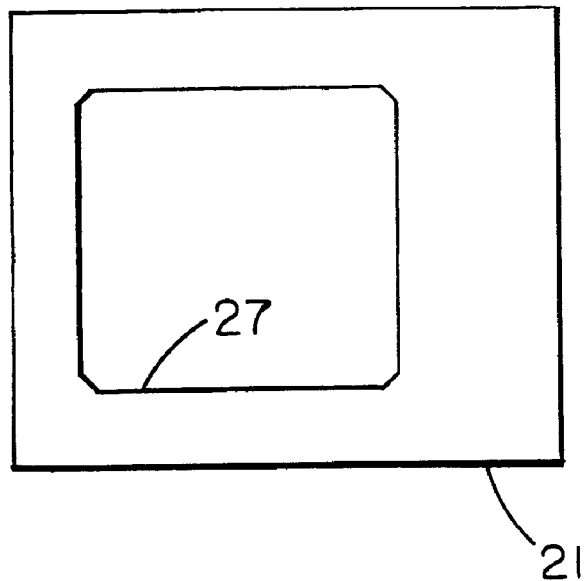
FIG. 1 is a plan view of a shim used in a novel sensor probe.

In one device, the membrane is bonded to an optional frame, shim 21 which is shown diagrammatically in FIG. 1. The outer dimensions of the shim match the outer dimensions of the membrane. The shim and membrane assembly 23 is then bonded to an elastomeric carrier 25 as shown in edge view in FIG. 2. The combination of the shim and the carrier provide support and protection for the relatively fragile membrane so that the membrane will be less likely to become wrinkled or creased. Alternatively, the membrane can be bonded directly to the elastomeric carrier.

Since the shim material is conducting and would interfere with measurements, an opening 27 is provided in the shim below the sensing region. To maintain the proper spacing, the opening is filled with an elastomer, a material which does not interfere with measurements.

Figure 2:
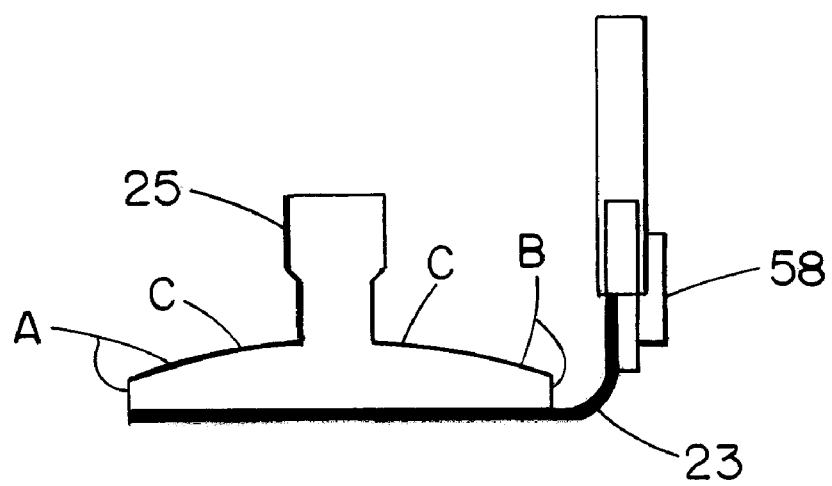
FIG. 2 is a side view of an elastomeric carrier with a sensor and the shim of FIG. 1 used in the novel probe.

When the membrane is to be brought into contact with the previously described convex surface, the assembly positioned above that surface and the assembly is aligned so that the highest straight line element (generatrix) of that developable surface is parallel to a line perpendicular to the plane of the paper in FIG. 2. The center of the membrane is then brought into contact with that highest element on that surface and the edges of the carrier which are shown as the left- and right-hand edges (A and B) in FIG. 2, are pressed downward toward that surface, causing the assembly to bend and conform to the curvature of the surface. The presence of the shim, which has a relatively high modulus of elasticity while the elastomeric carrier is made of a material which is chosen to have a low modulus of elasticity, causes the assembly to bend in such a manner that the membrane is subjected to negligible longitudinal compression so that it does not buckle or wrinkle.

As stated above, the membrane is to conform to a surface whose radius of curvature is almost constant (for each given sample) and the contact between the membrane and that surface must be uniformly intimate, implying approximately constant unit pressure over the contact area. The bending of the assembly in conforming to the surface is simple beam bending. The uniform pressure requirement constitutes uniform distributed loading along the beam length, and that, in turn, implies a parabolic bending moment distribution along the beam length. Such a moment distribution is inconsistent with constant bending radius of curvature in a beam having a constant section modulus.

The radius of curvature of the bending of the beam is proportional to the ratio of the section modulus of the beam cross section to the bending moment at that section. If, then, the bending radius of curvature is to be made constant (or nearly so) along the beam length, this ratio must be made constant over the useful length of the assembly which constitutes the beam. In the configuration shown in FIG. 2, this implies that the vertical thickness of the assembly must be varied along the beam length as shown at points C. The stiffness of the shim contributes a negligible amount to the section modulus, so analysis shows that the thickness of the carrier should theoretically be proportional to L to the $\frac{2}{3}$ power where L is the distance from the ends A and B. In the assembly, as designed, the ideal thickness variation is approximated by a two-segment straight-line taper as shown. This has proven to provide a good uniform contact on a constant curvature surface.

This assembly, without modification, can be pressed into uniform contact with either a cylindrical surface or a conical surface, by applying the forces shown at points A and B in FIG. 2.

FIG. 3 shows the previously described assembly mounted in a holder 10 which in turn, is retained in a case 16. The holder holds the assembly in alignment with the case so that the case can be used to apply the necessary downward forces at points A and B. The holder is free to slide up and down in the case to allow the membrane and its assembly to conform to the required curved surfaces. A button device 32 is provided so that, when desired, the holder can be restrained from sliding upward in the case and the membrane and its assembly can be pressed uniformly against a flat surface.

Figure 3A:
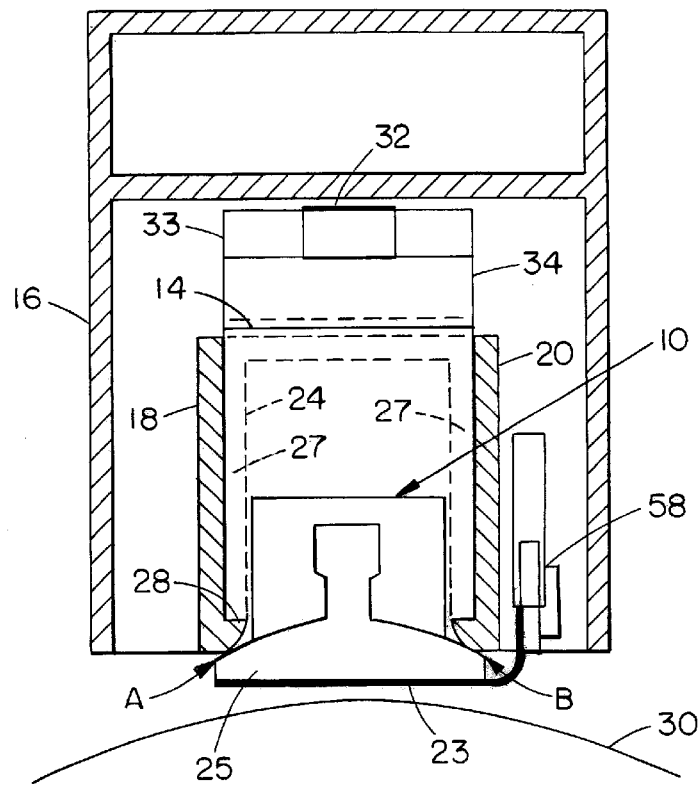
FIG. 3A is a cross-sectional view of the probe including the carrier, shim and sensor of FIG. 2.
Figure 3B:
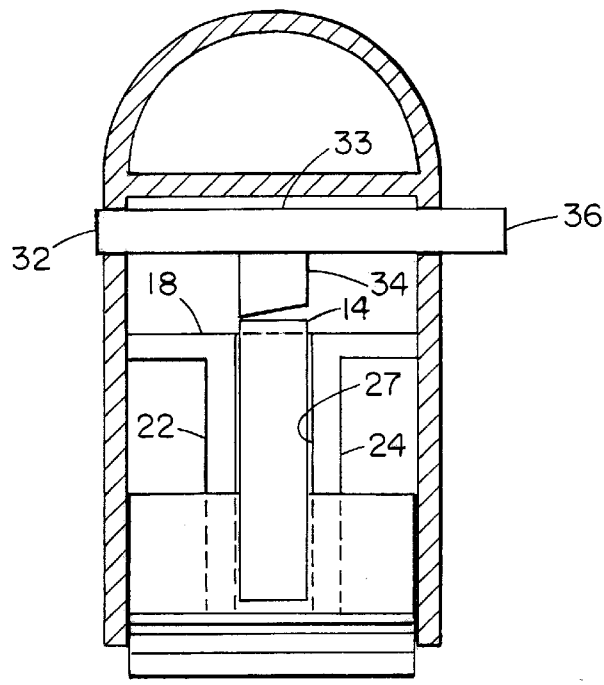
FIG. 3B is a cross-sectional view of the probe taken transverse to the view of FIG. 3A.
Figure 3C:
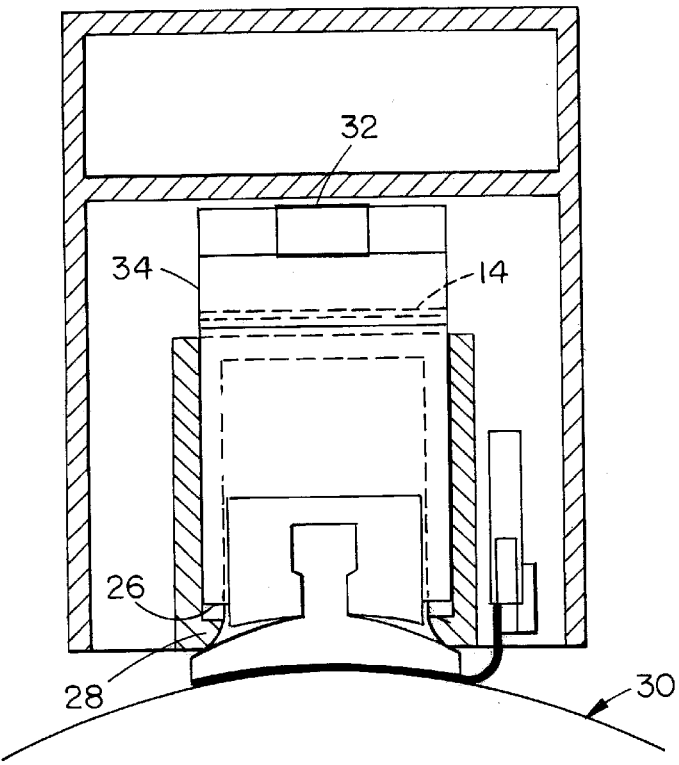
FIGS. 3C and 3D are views similar to FIGS. 3A and 3B, respectively, with the probe pressed against a convex surface.
Figure 3D:
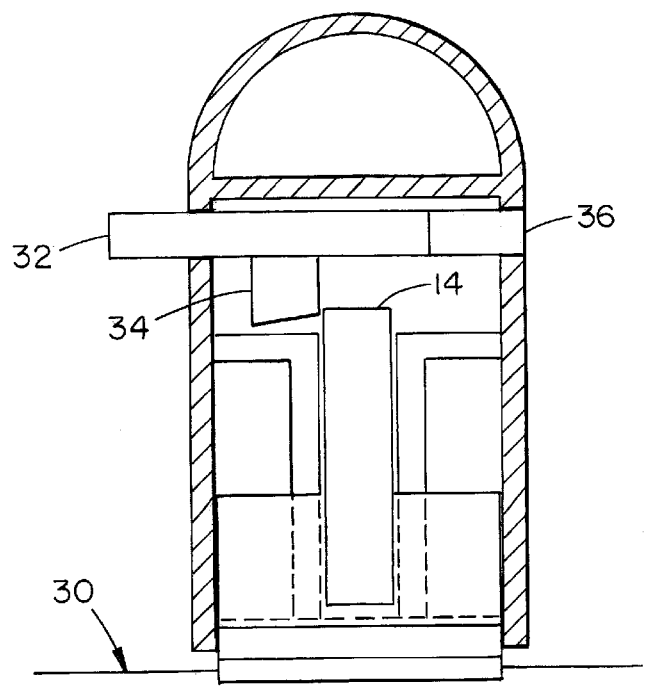
Figure 4A:
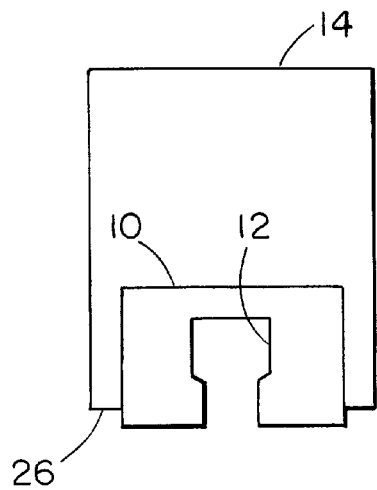
FIGS. 4A and 4B are views of the holder as oriented in FIGS. 3A and 3B respectively.
Figure 4B:
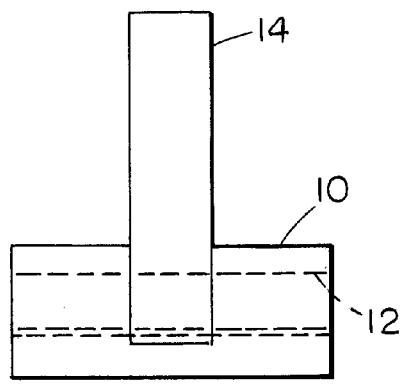

More specifically, the holder 10 for the carrier 25 is illustrated in FIGS. 4A and 4B. The holder is adapted to be aligned with a cylindrical test surface 30 such that the axis of the cylinder runs parallel to the length of the holder illustrated in FIG. 4B. A longitudinal slot 12 runs that length and captures the carrier 25. To guide the holder in its vertical motion, a guide plate 14 is fixed to the holder 10. That guide plate is adapted to ride in vertical slots within the case 16. Specifically, as illustrated in FIGS. 3A and 3B, two guide beams 18 and 20 extend across the narrow dimension of the case 16. Those beams 18 and 20 are spaced by the wide 1.3 inch dimension of the guide plate 14. Ridges 22 and 24 extend inwardly from each beam to form respective grooves 27 in which the guide plate travels. The lower edge 26 of the guide plate is stopped at its lowermost position by an abutment 28 extending from each of the beams. The lower surface of that abutment 28 is curved to press the elastomeric carrier against the test surface. Thus, as the probe is pressed against a cylindrical surface 30 illustrated in FIG. 3A, the center of the sensor membrane presses against the cylindrical surface. With applied pressure, the carrier 25 flexes and forces the holder upwardly within the case as illustrated in FIG. 3C. The guide plate 14 riding in the guide grooves 27 of the beams 18 and 20 assures appropriate alignment of the carrier and sensor.

As noted above, when sensing flat surfaces the holder may be retained in its lowermost position, when the flat faced elastomeric carrier shown in FIG. 2 is used. This assures that the sensor does not rise above the surface with any retained deformation of the carrier. To that end, a button 32 can be pressed to slide a carrier 33 to the right as viewed in FIG. 3B. The carrier carries an abutment 34 which moves into position over the guide plate 14 to retain the guide plate in its lowermost position. For use with curved surfaces, the opposite button 36 is pressed to move the abutment 34 to the left as in FIG. 3D out of alignment with the guide plate.

Figure 5:
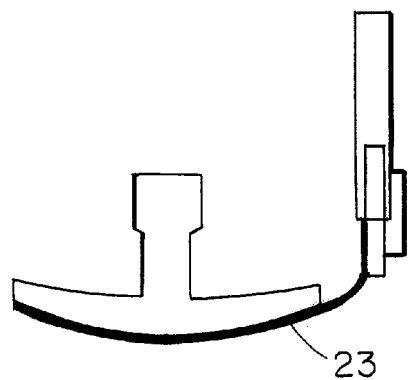
FIG. 5 is a view similar to FIG. 2 of an alternative carrier.
Figure 6A:
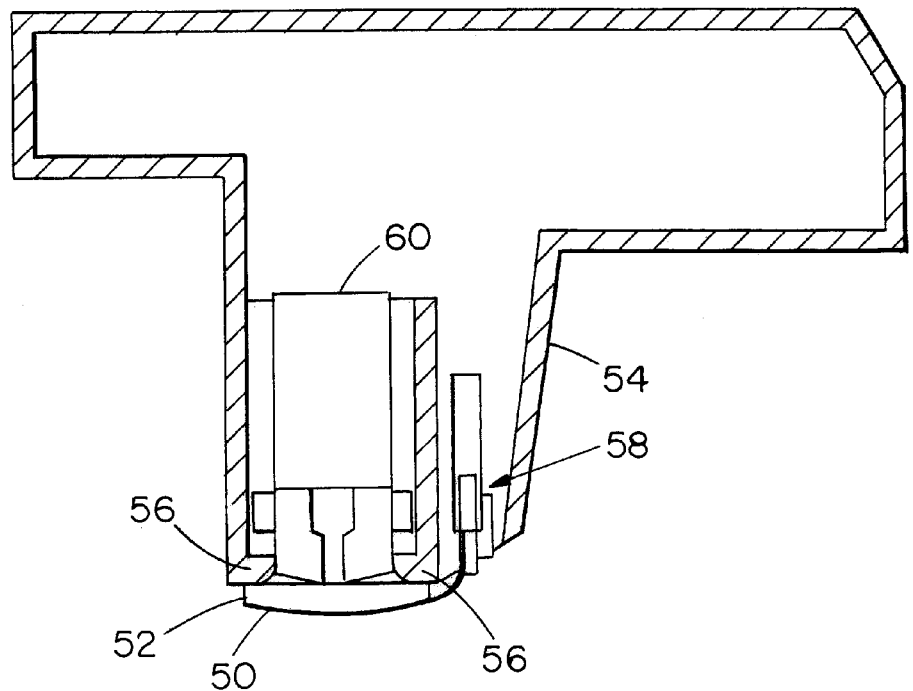
FIGS. 6A and 6B are longitudinal and transverse cross-sectional views of an alternative sensor probe embodying the present invention, with an elastomeric carrier that is formed with a convex surface to improve inspection of concave surfaces.
Figure 6B:
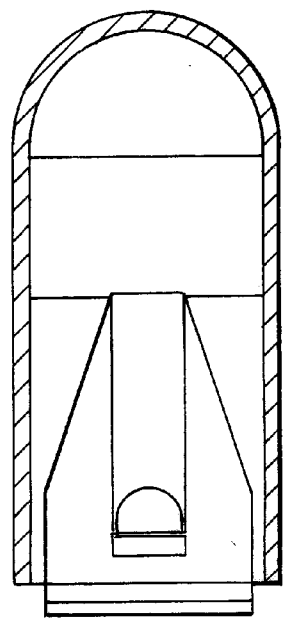

An alternative carrier for use with concave surfaces is illustrated in FIG. 5.

FIGS. 6 through 9 illustrate an alternative probe design which is suitable for concave, convex and flat surfaces as well as surfaces with tapers such as conical surfaces. Here, the lower surface 50 of the flexible carrier 52 is convex for positioning in concave surfaces, but is conformable to convex surfaces.

Figure 7A:
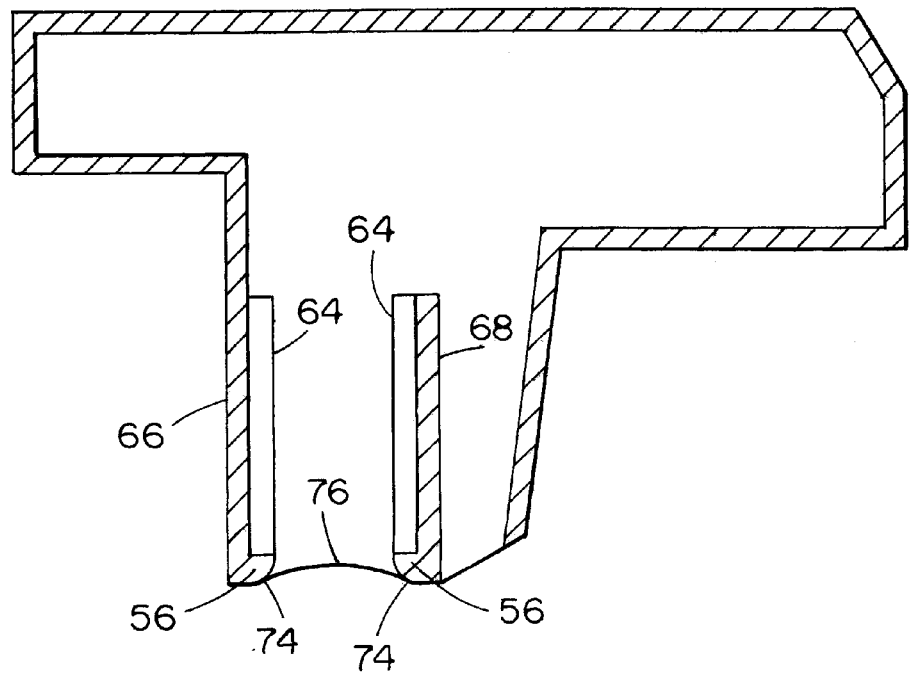
FIGS. 7A and 7B are longitudinal and cross-sectional views of the case of the embodiment of FIGS. 6A and 6B.
Figure 7B:
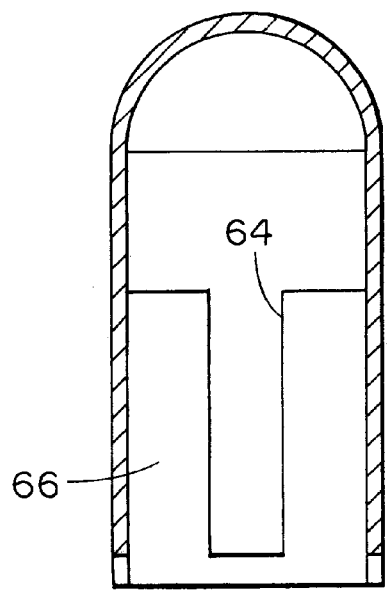
Figure 8A:
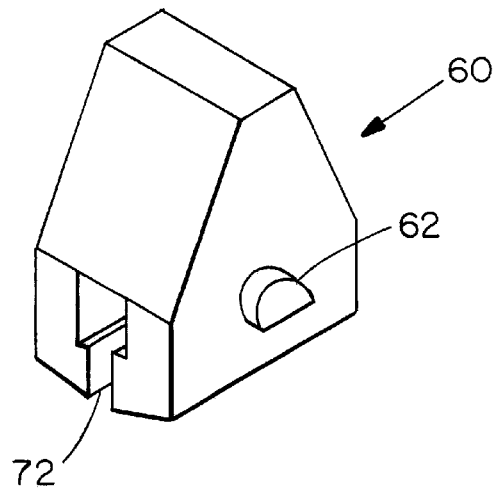
FIGS. 8A, 8B and 8C are perspective, end and side views, respectively, of a carrier holder in the embodiment of FIGS. 6A and 6B.
Figure 8B:
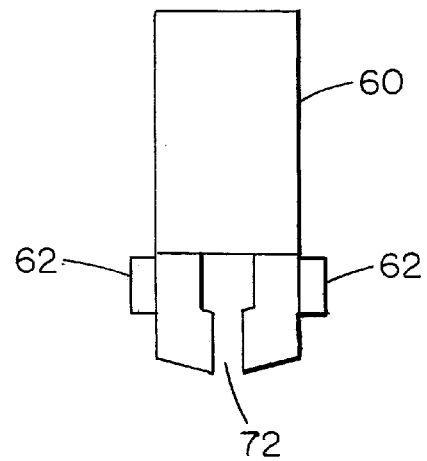
Figure 8C:
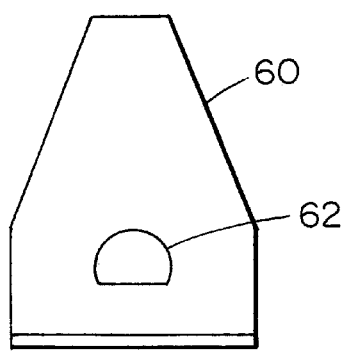
Figure 9A:
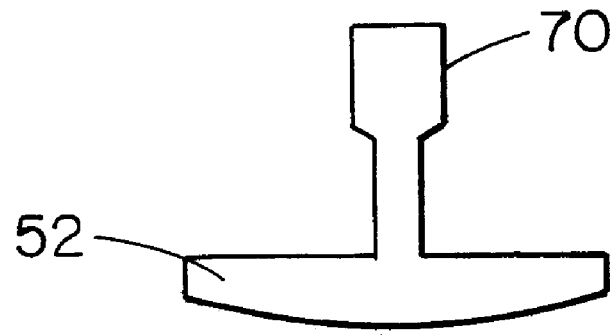
FIGS. 9A and 9B are end and side views of a flexible test circuit carrier in the embodiment of FIGS. 6A and 6B.
Figure 9B:
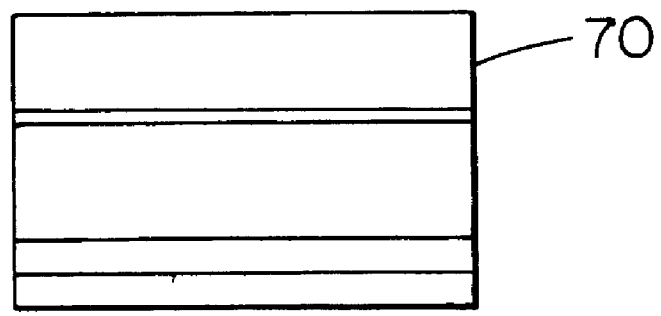

In this embodiment the casing has been redesigned as illustrated in FIGS. 7A and 7B and the holder has been redesigned as illustrated in FIGS. 8A, 8B and 8C to allow for both translational and pivotable movement. As before the carrier is translatable into the probe case 54, but abutments 56 press against the side edges of the carrier as the center region is pushed into the case, thereby producing a concave surface for positioning against a convex surface. The case abuts the carrier along curved surfaces 74 on abutments 56 at the lower ends of the walls 66 and 68. The case is curved at 76 at opposite ends of the carrier to provide clearance space for a convex test surface.

Rather than the guide plate of the prior embodiment, the holder has guide knobs 62 at opposite sides thereof. Those knobs translate vertically in respective grooves 64 formed in casing plates 66 and 68. By providing a pivoting action about the side to side axis of the knobs 62, one end of the carrier may, for example, be left in convex form, while the opposite end is pressed into the case to assume a flat shape. As before, a rib 70 of the carrier 52 is insertable into the slot 72 of the holder to retain the carrier 52. Further, the carrier 52 is thinner at its sides where it is abutted by the case, than at the center region.

As before, a connector assembly 58 is provided for providing electrical connection between the circuit on the membrane and an analyzer. Alternatively, leads from the analyzer can be directly bonded to the test circuit on the membrane, thus eliminating the connector 58.

Other configurations are well within one of ordinary skill in the art. For example, the abutments 28 could be aligned for conical or spherical rather than cylindrical surfaces. The entire probe could be reduced in size to a pencil configuration. The probe is also suitable for use with sensors other than the meandering winding magnetometer (MWM) illustrated. For example, it may be used with other quasistatic spatial mode (QSM) sensing devices such as the inter-digital electrode dielectrometer (IDED).

Figure 10B:
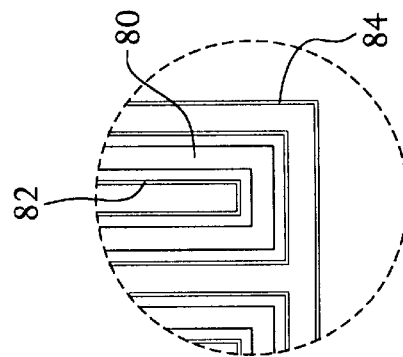
FIG. 10A is an illustration of one embodiment of sensor circuitry and FIG. 10B is an enlarged view of the circled portion of FIG. 10A.
Figure 10A:
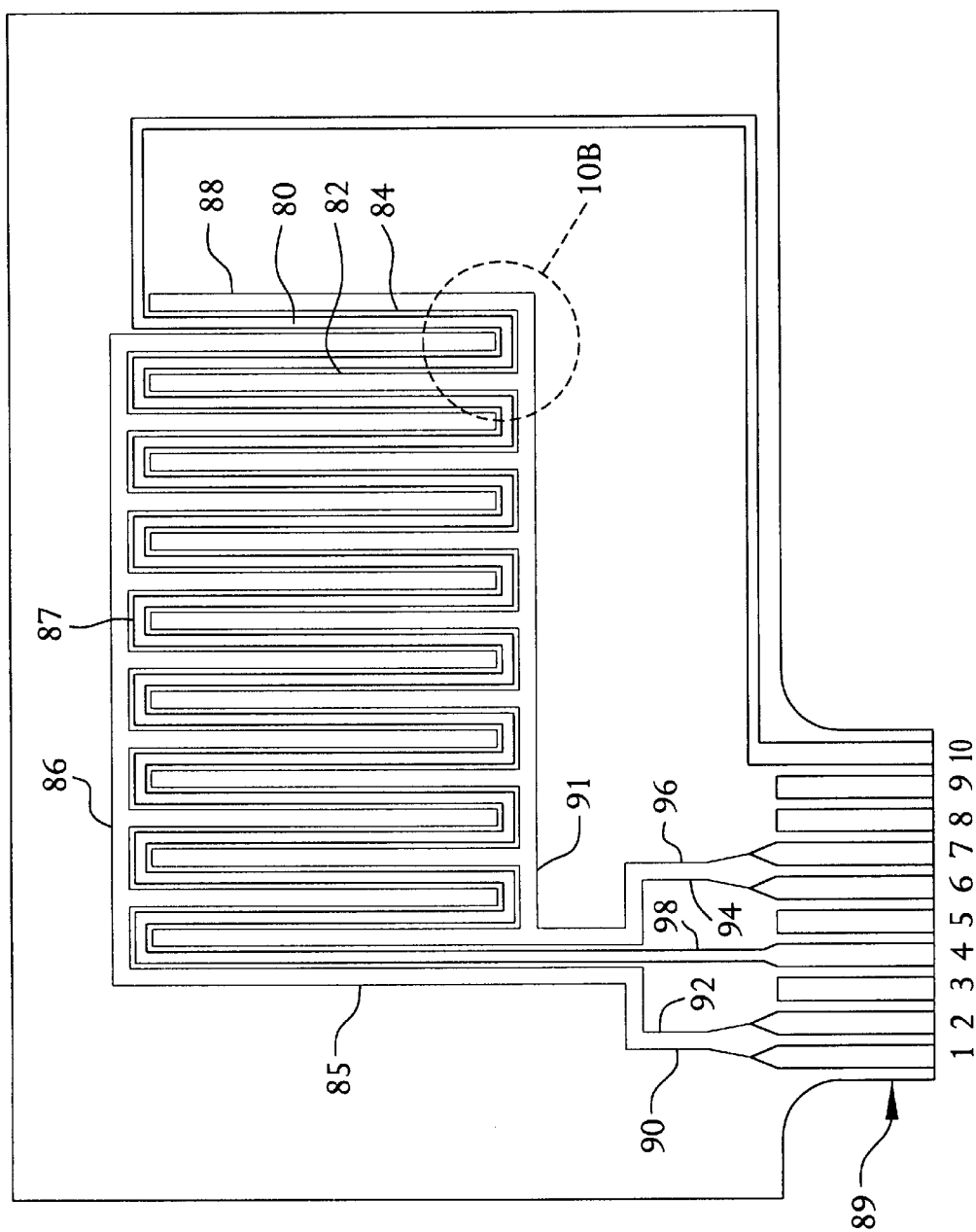

FIGS. 10A and 10B illustrate the sensor circuitry on the elastomeric membrane in one embodiment, with dimensions in inches shown. The preferred circuit is a copper conductor sandwiched between layers of nonconducting Kapton® material. In the preferred embodiment, the copper is deposited across one Kapton® surface, etched to form the circuit and covered with another layer of Kapton® material.

The circuit includes a meandering primary 80 which leads from contact 4 to contact 10. Secondary windings 82 and 84 lead from contacts 2 and 6 to parallel the primary through its meandering course. The secondaries are at equal distances from the primary to provide equal coupling of flux and to cancel unmodelled flux. At the end of the meandering course, the secondary which originated at contact 2 extends along the upper and left sides of the coil to contact 1. The secondary which originated at contact 6 extends along the right and bottom sides of the coil to contact 7. All contacts are connected through an electrical connector 38 (FIG. 3A) to an HP4285 LCR meter, or an alternative impedance measurement instrument, where contacts 2 and 6 may be electrically connected and contacts 1 and 7 may be electrically connected. Contacts 2 and 6 may be tied to ground, and voltage measured at contacts 1 and 7. This parallel connection minimizes capacitive coupling and thus results in an improved high frequency response. Alternatively, the sensing windings may be connected in series for a larger output signal.

Figure 11:
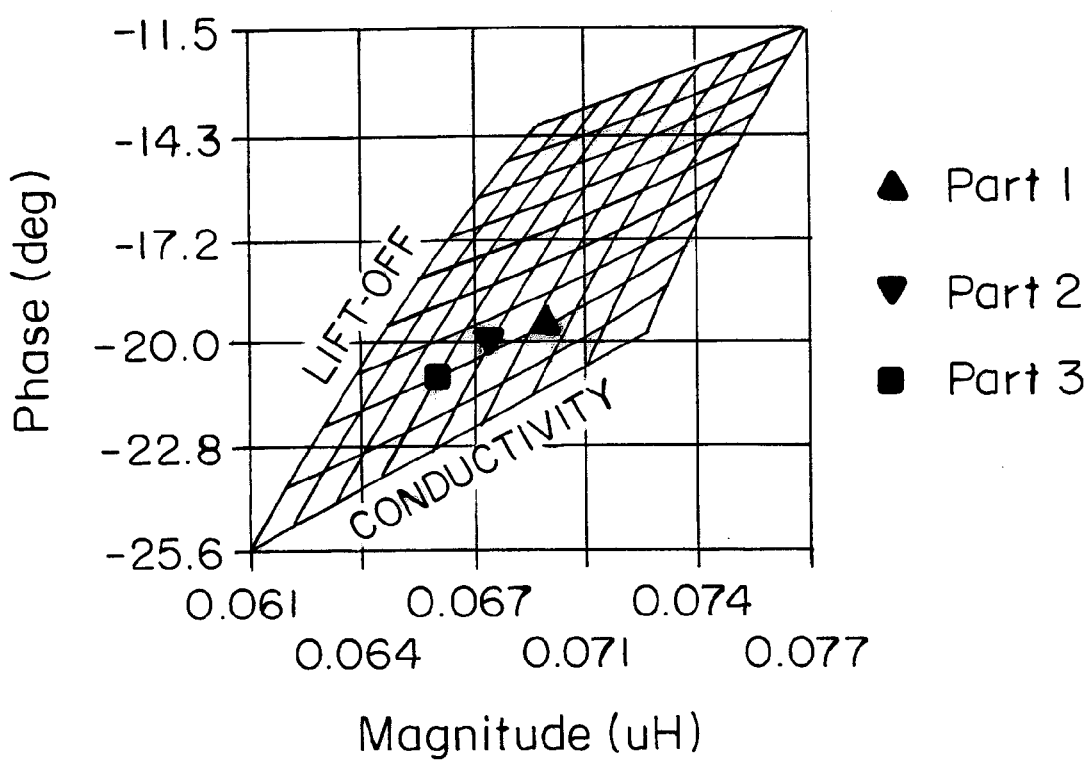
FIG. 11 illustrates a measurement grid resulting from use of the circuitry of FIG. 10A.

The extended vertical portions of the windings establish an electromagnetic field in the test surface having a spatial wavelength equal to twice the center-to-center distance between the extended lengths of the primary winding. The sensing windings sense the response of the test substrate to the imposed electromagnetic field. As taught in U.S. Pat. No. 5,453,689, response of different substrates to the periodic waveform is modelled to define a property estimation grid such as illustrated in FIG. 11 which estimates properties of the test surface from sensed impedance magnitude and phase from the sensing windings.

The horizontal connecting portions of the windings in FIG. 10A which connect the extended vertical portions are unmodelled regions, so sensor signals from those regions should be minimized. The coupling between elements of the sensing windings and the primary winding is a function of the spacing between the winding elements. Accordingly, in order to minimize the coupling along the unmodelled end portions of the winding, the terminal sensing leads 86 and 88 which return to the connector 89 closely parallel the extended lengths at the ends of the array and the connecting portions of the respective windings. The spacing is kept as small as is practical in fabricating the circuit and is preferably less than one quarter wavelength.

For example, the terminal lead which extends from winding 82 returns along a length 86 parallel to and closely spaced from connecting portions 87 of that same secondary winding along a length 86. It then runs along the length 85 which is parallel to and closely spaced from the first extended length of that winding along a portion 85. Finally, the pair of terminal leads to the winding are closely spaced and parallel along lengths 90 and 92 which are displaced from the terminal lead 98 of the primary winding. Similarly, the terminal lead from secondary winding 84 extends parallel and close to the final extended length of that winding along a portion 88, parallel and close to connecting portions along a length 91, and close to and parallel to the other terminal lead of the same winding along lengths 94 and 96 displaced from the primary terminal lead 98.

To further reduce the coupling in unmodelled regions of the array, a conductive shield plane may be provided in a layer parallel to the circuit over the unmodelled regions. Most preferably, a shield layer is provided both above and below the unmodelled coupling regions. A window in the shield which exposes the sensing region is provided within the region indicated by broken lines in FIG. 14A.

Application software utilizes "measurement grids" of one or more dimensions to translate independent instrument measurements of impedance (magnitude and phase) into estimates of the electrical properties and the thickness of the layers of the material being measured. Each grid dimension is associated with one unknown property, such as electrical conductivity or layer thickness. For each measurement data point (magnitude and phase), the grid table is searched to find the pre-computed values for the unknown properties that are closest to the actual measurements. In a two-dimensional grid, for example, the nearest four points would be located. The software then calculates an estimate for one or more of the properties using mathematical interpolation techniques.

FIG. 11 shows a two-dimensional measurement grid with unknown properties (1) electrical conductivity and (2) lift-off. A grid point is located at the intersection of each pair of grid lines. Three sets of "measurement data points" taken from sensor impedance magnitude and phase are also represented by the sets of squares and two sets of triangles. Each set contains 5 measurements that are coincident in the figure because of high measurement repeatability.

Grid tables can be of one, two, three or more dimensions. For example, grid tables of one dimension can include estimates of electrical conductivity varying by frequency, or a dependent property such as porosity varying by frequency. Two-dimensional grids can include, but are not limited to, estimates of (1) electrical conductivity and lift-off (defined to be the distance between the sensor and the material under test); (2) electrical conductivity and layer (or coating) thickness; (3) layer thickness and lift-off; (4) magnetic susceptibility and electrical conductivity; or (5) the real part of the magnetic susceptibility and the imaginary part of the magnetic susceptibility. Two examples of three-dimensional grids are (1) electrical conductivity, lift-off, and layer thickness and (2) electrical conductivity, magnetic susceptibility, and lift-off. These three-dimensional grids require that multiple measurements be made at different lift-offs or with multiple sensor geometry configurations or that a series of two-dimensional grids such as those listed above, be calculated for different operating frequencies, sensor geometries, or lift-offs.

Environmental conditions, such as the temperature of the material being measured or a reference part used for calibration, may be monitored and recorded while making measurements. The environmental conditions existing at the time of measurement may affect some of the electrical properties being measured.

Correlation of the estimated electrical properties with secondary properties of interest can be performed by defining a relationship between the electrical properties and the secondary properties. This relationship can be used to translate estimated properties such as electrical conductivity, layer thickness and lift-off into estimates of surface roughness, plastic deformation, fatigue damage, corrosion, porosity, temperature and others. It has been shown that electrical conductivity correlates with (1) porosity of thermal spray coatings, (2) fatigue in stainless steel, (3) plastic deformation in aluminum and titanium, and (4) temperature. It has also been shown that lift-off correlates with surface roughness. It has also been shown that permeability varies with applied or residual stress for carbon steel.

Anisotropic conductivity and permeability have also been measured by rotating the meandering winding about an axis perpendicular to the inspection surface. This has been used to determine crack orientations in stainless steel, and to find direction of maximum applied loads or cumulative strain in carbon steel.

Estimation of electrical and geometric properties, as well as correlation with secondary properties, can be performed in "real-time" (concurrently with making the magnitude and phase measurements) or can be performed at some later time using stored data measurements.

Measurement grids can be calibrated using measurements in air or on reference parts. The objective is to vary at least one of the "unknown" properties during calibration to ensure that the measurement grid is correctly aligned. For example, in a conductivity/lift-off grid, the lift-off can be varied during calibration, using shims of known or unknown thickness. This will establish the correct orientation for the grid. Parameters in the forward models of the sensor response, such as the effective area of the sensing region, can then be adjusted to orient the grid correctly. Also, offsets or scale factors due to instrument drift or uncalibrated behavior can be computed and used later to shift the measurement data. In addition, the conductivity might be varied during calibration or as part of a measurement procedure to establish the orientation of a line of constant lift-off. By varying the part temperature the conductivity will vary with the lift-off remaining constant. For other grid types, such as a conductivity permeability grid, the permeability might be varied during calibration by applying a bias magnetic field. This would permit alignment of the lines of constant conductivity (along which only the permeability will vary). During measurement procedures it is also desirable to make multiple measurements at multiple operating conditions including multiple liftoffs, temperatures, or bias fields, to permit averaging of unknown property estimates, as well as to permit estimation of more than one unknown property.

Figure 12:
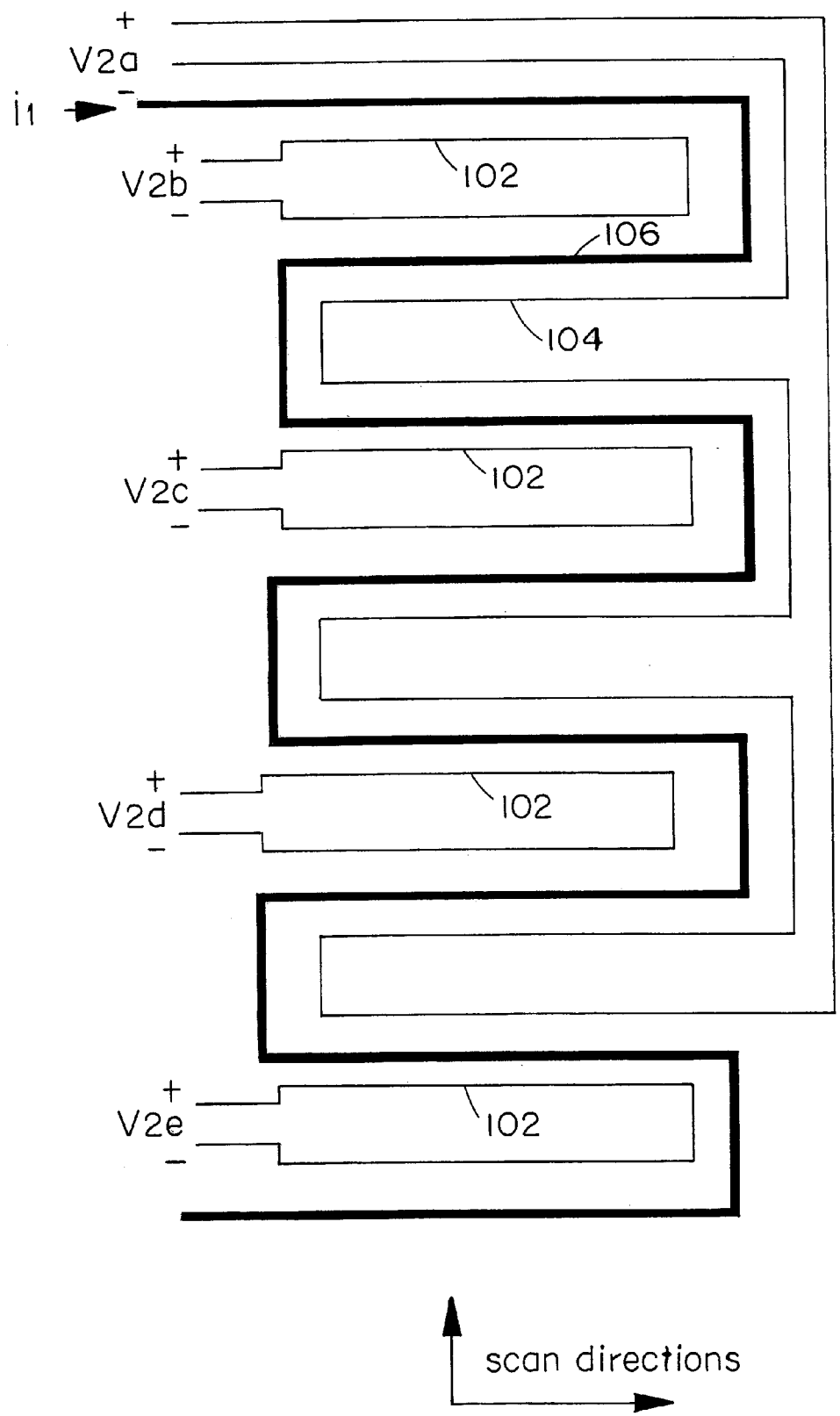
FIGS. 12–15, 16A, 16B and 17 illustrate alternative sensor circuits.

FIGS. 12–17 describe alternatives to the sensor geometry shown in FIG. 10A. FIG. 12 illustrates the breaking up of one secondary into regions with single meanders. Such single meander structures have been disclosed in U.S. Pat. No. 5,453,689. By including several single meander structures 102, having voltage output, $V_{2b}$–$V_{2e}$, in FIG. 10, in the same sensing region as a multiple meander secondary 104, (V2a) on the opposite side of the primary winding 106, a profile of electrical property variations within the sensor footprint can be provided. The inclusion of the multiple meander secondary permits measurement of the average properties over the entire footprint and can be used to normalize or provide a reference value for the estimation of absolute electrical properties.

Figure 13:
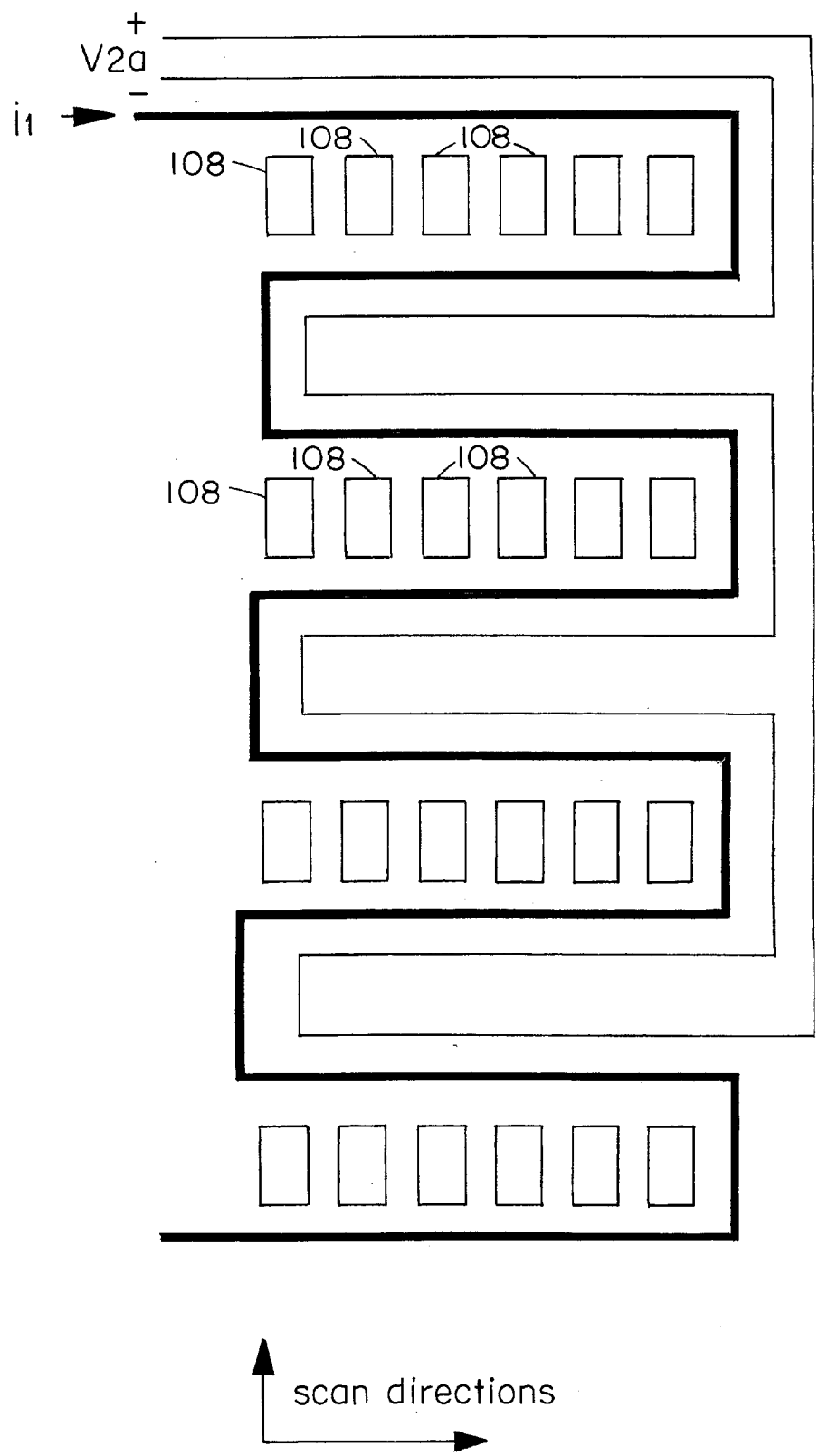

FIG. 13 illustrates that the individual sensor regions might be further broken into sub-regions 108 within each meander.

The use of such sensor arrays separate from a meandering winding magnetometer is widespread throughout the literature. The unique approach disclosed here is the integration of such a sensor array within a meandering structure that is easy to model and with a secondary winding with multiple meanders that permits measurement and referencing to an average property over the entire sensing region. The small rectangular secondaries 108 might be super-conducting SQUID type sensors, Hall effect probes, magneto-resistive sensors or wound eddy current sensor type coils. These sensors may be in the plane as shown or perpendicular to the plane at the same location to measure other directional field components.

Figure 14:
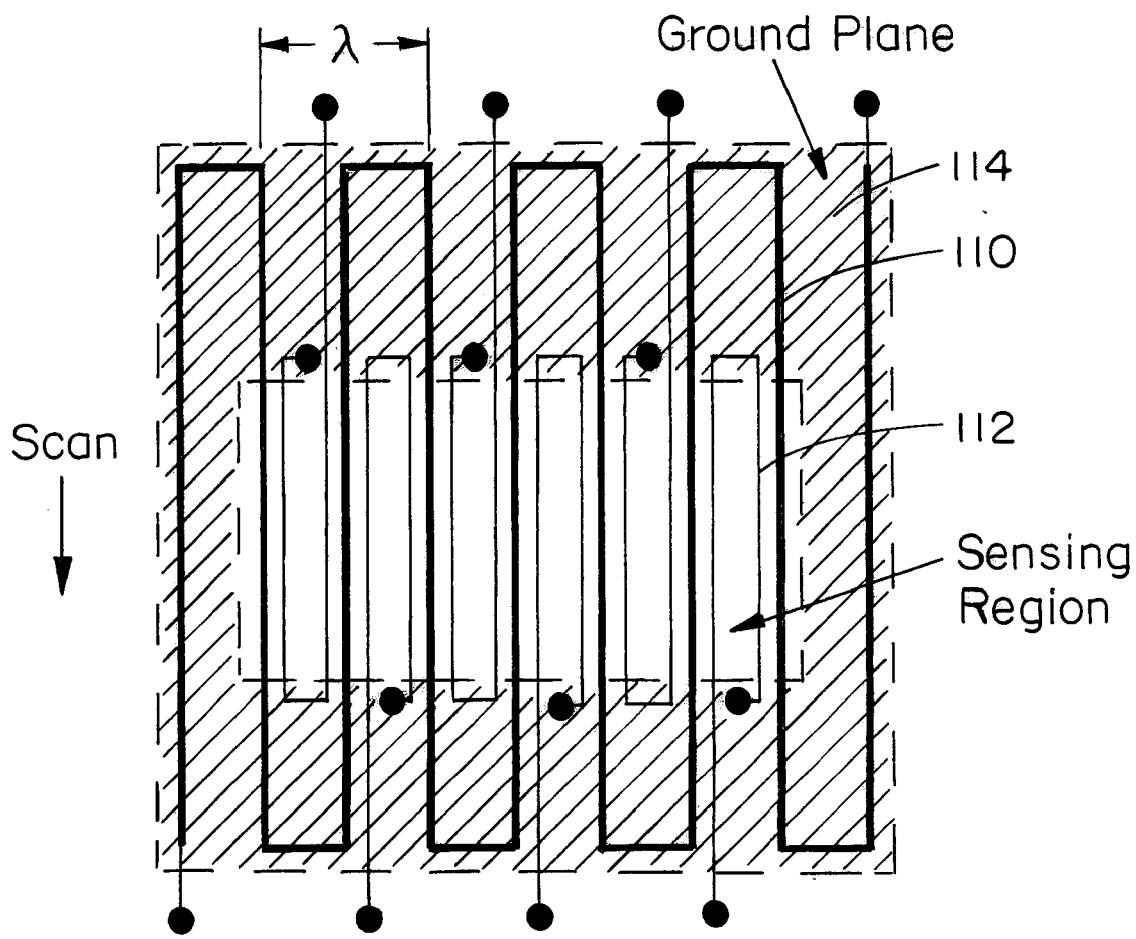

FIG. 14 illustrates an embodiment in which both secondary windings are broken into individual coils. As in previous embodiments, the primary winding 110 meanders in a square wave pattern. The sensing elements 112 are individual rectangular winding loops. This sensor array can be distinguished from prior individual loop arrays in that the spatial periodicity of the primary winding establishes a spatially periodic electromagnetic waveform which can be readily modelled, and the model can be based on the coupling between all primary and secondary windings within the sensing region. The loops are equally spaced within the primary winding to provide symmetry which can be readily modelled to provide high resolution surface property measurement. Rather than attempting to decouple the various sensing elements, coupling is designed into the array and is considered in the model.

As before, connecting portions of the primary winding illustrated at the top and bottom of the array in FIG. 11 are unmodelled portions. To minimize coupling of the secondary loops to those portions, the top and bottom ends of the secondary loops are formed at least one wavelength inside of the connecting portions. Further, a shield plane is formed above and/or below the sensing plane in the unmodelled regions. As illustrated in FIG. 14, the shield plane is between the broken lines on planes above and below the sensing array. The sensing region is within the shield plane.

Figure 15:
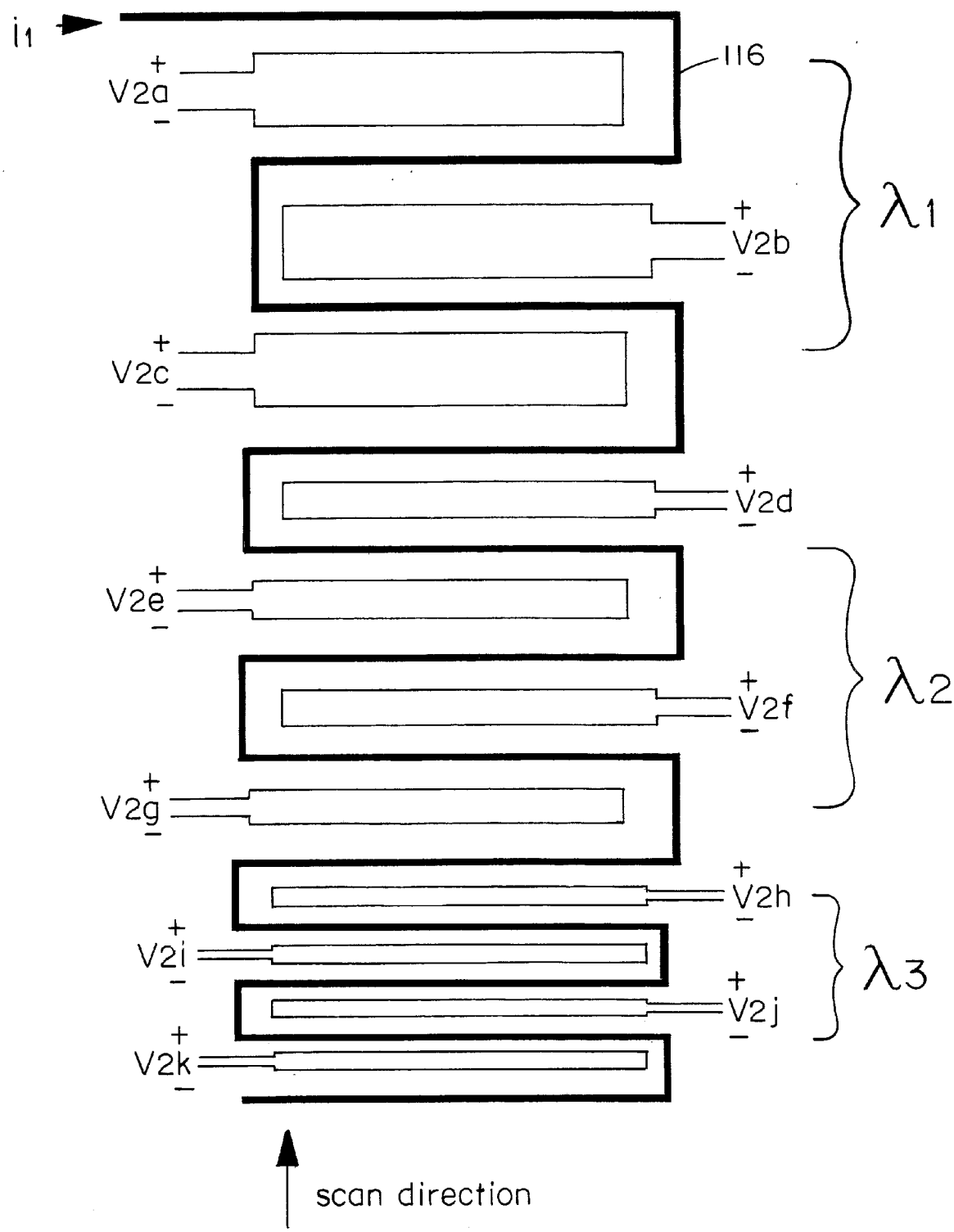

FIG. 15 illustrates another sensor design that is similar to FIG. 14, except that a multiple wavelength winding geometry is included within a single sensor. Specifically, primary winding 116 has regions of different wavelengths $\lambda 1$, $\lambda 2$ and $\lambda 3$. The represents an enhancement to the methods and apparatus described in U.S. Pat. 5,015,951. It is best to skip a wavelength between regions with different wavelengths to avoid unmodelled coupling.

Figure 16A:
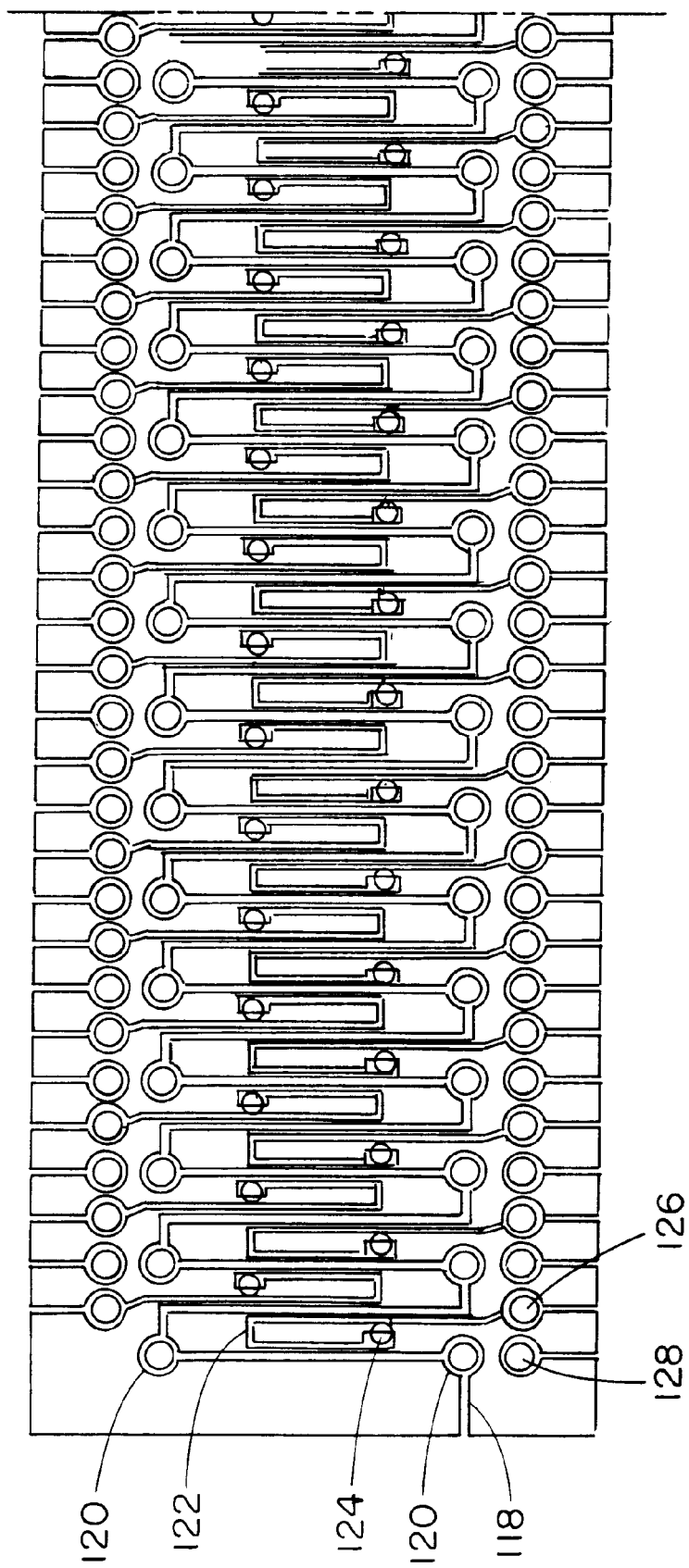
Figure 16B:
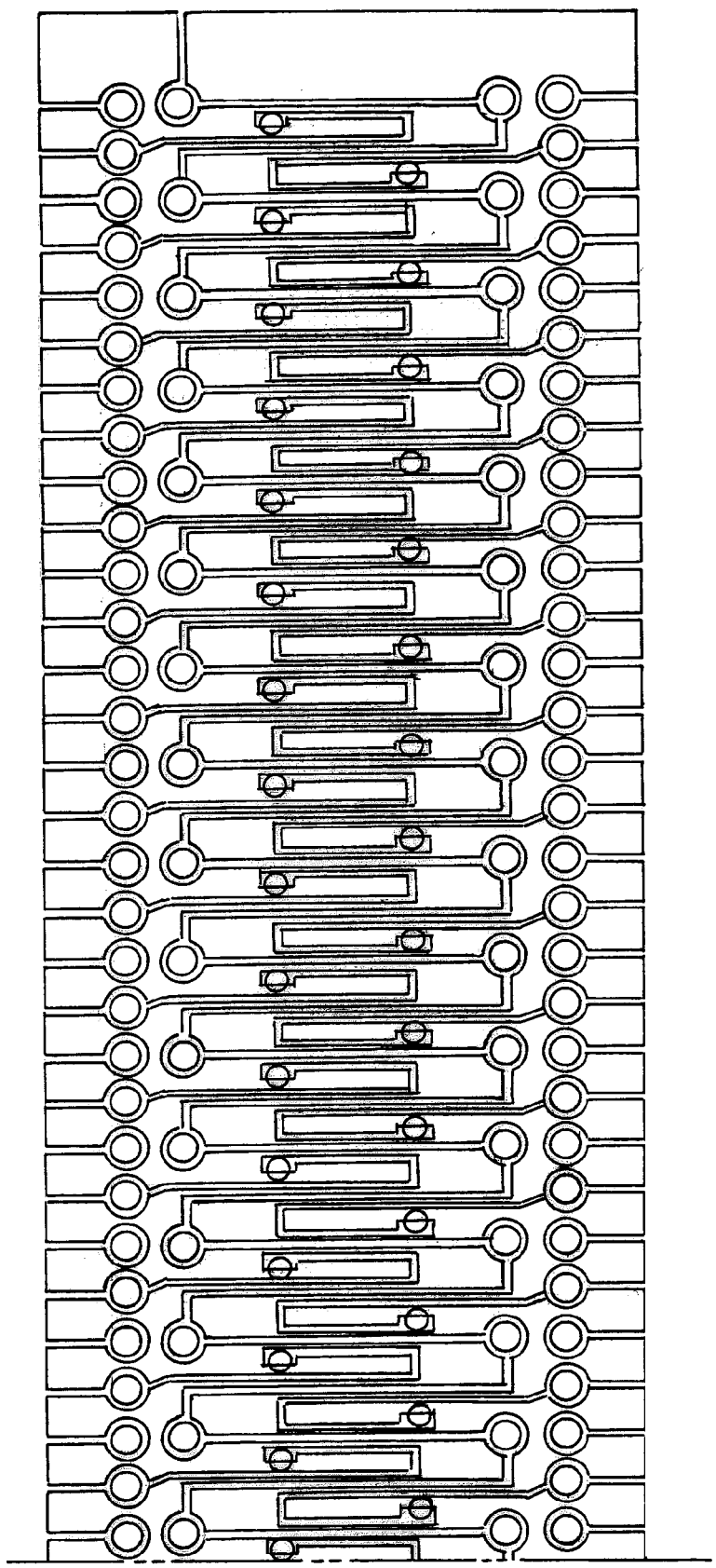

FIGS. 16A and 16B illustrates an extension of the individual loop design of FIG. 14 to an adhesive tape which may be packaged as a roll of tape. Individual lengths of the tape may be cut to meet the length requirements of particular applications. As before, this embodiment includes a conductive pattern 118 which forms a meandering primary winding. This primary winding includes connecting pads 120, such as solder pads, at wavelength spacings. Accordingly, the tape may be cut at any wavelength with bonding pads being available for connecting an analyzer to the primary. Similarly, each sensing loop 122 has respective bonding pads 124 and 126. Additional bonding pads 128 may, for example, provide connection between a shielding layer and ground. Connection to the bonding pads may, for example, be by soldering of wires from twisted pairs of shielded cable. Adhesive is provided along one surface of the supporting membrane to bond the selected length of sensor array to a part to be tested.

As before, a space of at least one wavelength between the loops and the connecting portions of the primary winding minimizes unmodelled inductive and capacitive coupling.

Other embodiments, such as those of FIGS. 10A, 12, 13 and 14 may also be implemented on adhesive tape.

In general, the various arrays allow for imaging of a surface property along one dimension which extends a length of the surface through multiple spatial wavelengths. By applying signals of multiple frequencies to the primary winding or by providing an array with different spatial wavelengths as in FIG. 15, a second dimension, depth of penetration, can be added to that image. By scanning an array, as in the direction indicated in FIG. 14, a third dimension can be added to the image.

Figure 17:
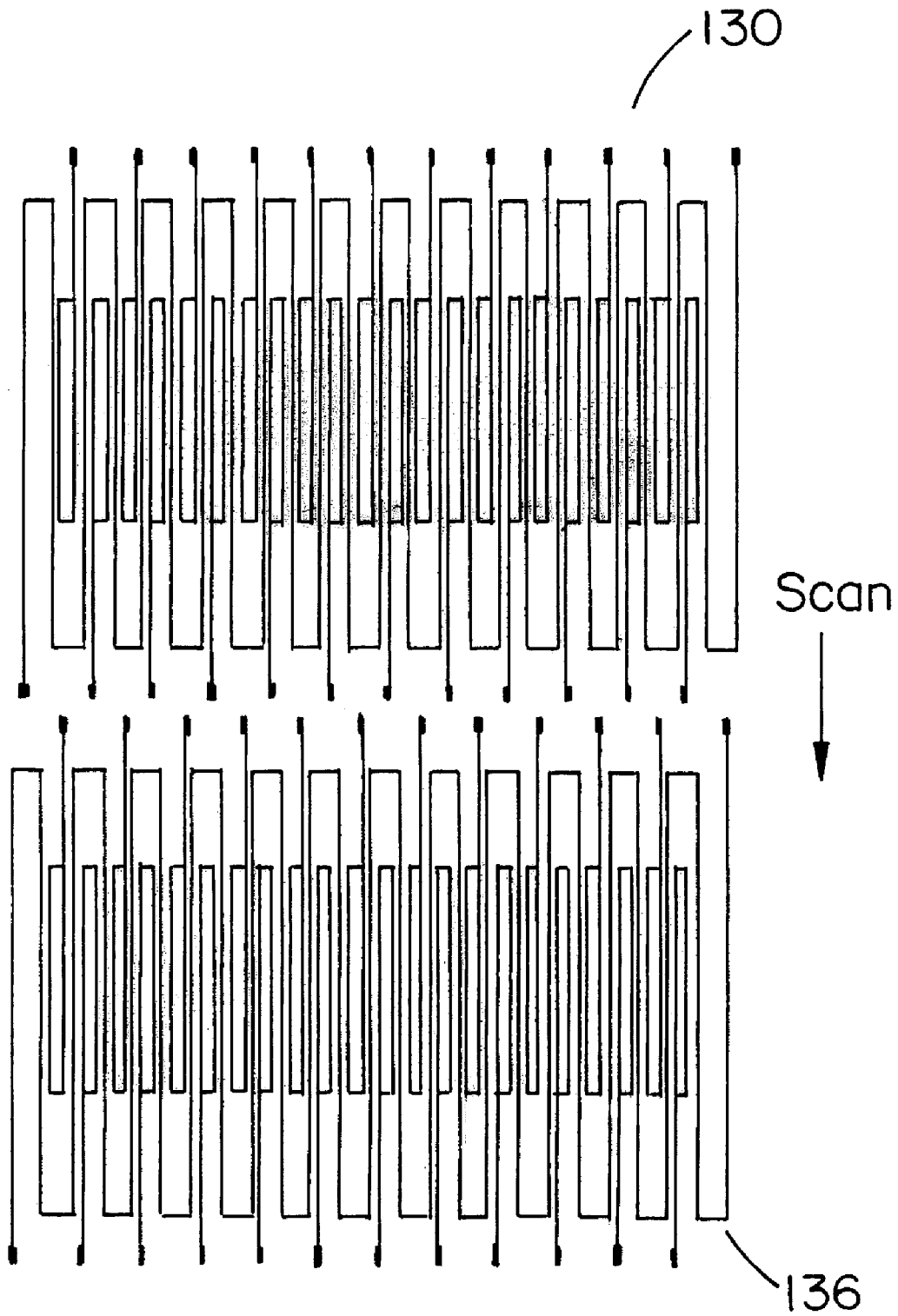

To increase the resolution across the first dimension with scanning in that third dimension, the dual array of FIG. 17 may be used. Here, the arrays 130 and 136 are offset by one quarter wavelength, so that the second array fills in any detail missed by the first array. Conventional image enhancement techniques may be used in any of the image dimensions.

The sensor can be used in coating characterization applications for metals, intermetallics, ceramics, etc., in age degradation monitoring for fatigue, corrosion, wear, etc., and in material state monitoring such as residual stress, porosity and temperature, and for crack detection and size and depth determination.

Of particular note in these applications is the detection of fatigue prior to the initiation of cracks in a part. In conductive members, the conductivity of the part can be monitored. Although it is preferred that the meandering wave magnetometers described above and in U.S. Pat. No. 5,453,689 which use a measuring grid based on a model be used, other thin flexible probes such as EDED probes, particularly those conforming to the surface can be used.

By moving the probe across a test surface or providing an array of probes, spatial changes in electrical properties may be measured across the test surface to identify regions exposed to higher symptoms of aging such as stress or thermal fatigue.

Another significant application is that of roughness measurement. It has been determined that the average liftoff measurement which may be obtained using an MWM can be directly correlated to roughness measurements in either RMS roughness values or $R_A$ values. Roughness and conductivity measurements may be obtained independently using the modelled measuring grid. Other sensors which can be used for roughness measurements include a flat spiral winding and the IDED sensor. The footprint of the sensor should be large relative to the roughness dimensions in order to obtain an average across the test surface. Elements of the sensor should traverse a significant portion of the surface.

Yet another novel application of the MWM and IDED QSM sensors is that of porosity measurement. Electromagnetic properties can be measured by the MWM sensor to provide an indication of porosity. It has been demonstrated that conductivity provides such an indication and magnetic permeability of magnetizable materials may provide a similar indication. For non-conductive material such as ceramics, the dielectrometer of U.S. Pat. No. 4,814,690 may provide a permativity measurement which provides an indication of porosity. For some materials, a combination of MWM and dielectrometer measurements may be used.

Yet another novel application of the MWM and IDED is anisotropic property measurement as discussed earlier.

The device as shown and described herein is suitable for being held in the hand and manually pressed against the surface to which the membrane must conform. The device could also be easily incorporated into a mechanism by which force on a foot pedal, force applied by a pneumatic or hydraulic actuator, or force applied by an electromagnetic actuator could be used to press the membrane against the surface of a test object which was held in a suitable fixture.

The device as depicted herein provides a robust support for the membrane and its associated pattern while providing means for causing the membrane to uniformly contact curved developable surfaces. This configuration uses a minimum of moving parts, avoids the possibility of leaking bladders and has no need for external fluid supply.

The disclosed probe enhances the prior techniques presented in U.S. Pat. Nos. 4,814,690, 5,015,951 and 5,453,689. This probe and the previously presented sensors can be used in novel applications as well. These applications and alternative designs are presented in greater detail in each of the following documents which are incorporated herein in their entireties by reference:

A. Goldfine, N. et al., "Materials Characterization Using Model Based Meandering Winding Eddy Current Testing (MW-ET)," ERPI Topical Workshop: Electromagnetic NDW Applications in the Electric Power Industry, Charlotte, N.C., Aug. 21–23, 1995.

B. Goldfine, N., "Real-Time, Quantitative Materials Characterization Using Quasistatic Spatial Mode Sensing," presented at 41st Army Sagamore Conference, Aug. 29, 1994.

C. Goldfine, N., et al., "Dielectrometers and magnetometers, suitable for in-situ inspection of ceramic and metallic coated components," presented at SPIE Conference, Nondestructive Evaluation of Aging Infrastructure, June 1995.

D. Goldfine, N., "Application of the Meandering Wire Magnetometer to Detection and Quantification of Cummulative Fatigue Damage in Aircraft Structural Components," Small Business Innovation Research (SBIR) Topic Number N95-033 Phase I Program Proposal, Jan. 12, 1995 and Phase II Program Proposal, Apr. 17, 1996.

E. Goldfine, N., "Nondestructive Characterization of Fatigue Damage and Material Toughness in Structural Metals," Small Business Innovation Research (SBIR) Program Proposal, Topic Number N95-225, Jul. 6, 1995.

F. Goldfine, N., "Nondestructive Characterization of Thermal Spray Coating Porosity and Thickness," NASA SBIR Solicitation 94-1-Phase II 04.06 5552, Jun. 2, 1995.

G. Goldfine, N., "Application Of The MWM To In Situ Determination Of Age Related Degradation," Phase I final report and Phase II proposal dated Jan. 16, 1995 for Department of Energy Grant DE-FG0294ER81792.

H. Goldfine N., "MWM Array Characterization of Widespread Fatigue Damage Onset," Small Business Innovation Research Program Proposal Topic Number 96-FA4, May 1, 1996.

I. Goldfine N. et al. "Near Surface Material Property Profiling For Determination of SCC Acceptability," Fourth EPRI Balance of Plant Heat Exchanger NDE Symposium, Jackson Hole, WY, Jun. 10–12, 1996.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A test circuit comprising:

a meandering primary winding for imposing a spatially periodic magnetic field in a test substrate, the winding having extended portions across a sensing region and connecting portions connecting adjacent extended portions;

at least one meandering sensing winding having an extended length parallel to the extended portions of the primary winding;

terminal leads providing a pair of connections to each of the primary and sensing windings, leads from the at least one sensing winding being closely parallel at a terminal end and one of the first and second leads including a return length which closely parallels an outer extended length of the sensing winding; and a substrate for carrying the meandering primary winding, the meandering sensing winding, and the terminal leads.

2. A test circuit as claimed in claim 1 wherein the return length is spaced less than one quarter wavelength from the outer extended length of the sensing winding.

3. A test circuit as claimed in claim 1 comprising first and second meandering sensing windings on opposite sides of the primary winding, terminal leads from each sensing winding being closely parallel at a terminal end and including a return length which closely parallels outer extended length of the sensing winding.

4. A test circuit as claimed in claim 3 wherein pairs of terminal leads to the respective sensing windings are positioned substantially the same distance to either side of a terminal lead to the primary winding.

5. A test circuit as claimed in claim 4 wherein first and second terminal leads to the primary winding are substantially displaced from the terminal leads of the sensing winding.

6. A test circuit as claimed in claim 5 wherein the terminal leads of the primary windings are spaced at least one wavelength from the terminal leads of the sensing windings and the terminal leads to each sensing winding are spaced less than one quarter wavelength from each other.

7. A test circuit as claimed in claim 5 further comprising shielding over the connecting portions and terminal leads of the test circuit.

8. A test circuit as claimed in claim 1 wherein first and second terminal leads to the primary winding are substantially displaced from the terminal leads of the sensing winding.

9. A test circuit as claimed in claim 8 wherein the terminal leads to the primary winding are displaced at least one wavelength from terminal leads to the sensing winding.

10. A test circuit as claimed in claim 1 further comprising shielding over the connecting portions and terminal leads of the test circuit.

11. A test circuit as claimed in claim 1 wherein the outer portions of the sensing winding include a first extended length of the sensing winding and connecting portions of the sensing winding.

12. A test circuit as claimed in claim 1 comprising first and second meandering sensing windings on opposite sides of the primary winding, terminal leads to each sensing winding including a return length which closely parallel a first extended length of the winding and connecting portions of the sensing winding.

* * * * *